United States Patent [19]
Hernandez

[11] Patent Number: 5,823,938
[45] Date of Patent: Oct. 20, 1998

[54] MAGNETIC EYELID OCCLUDING APPARATUS

[75] Inventor: Edward V. Hernandez, Elk Grove, Calif.

[73] Assignee: The Regents Of The University Of Calfornia, Oakland, Calif.

[21] Appl. No.: 832,298

[22] Filed: Mar. 27, 1997

[51] Int. Cl.⁶ .................................................. A61N 1/00
[52] U.S. Cl. ............................ 600/15; 606/213; 606/216
[58] Field of Search .................................. 600/15, 12, 9; 602/78; 606/216, 215, 214, 213; 220/230

[56] References Cited

U.S. PATENT DOCUMENTS

| | | | |
|---|---|---|---|
| 3,626,940 | 12/1971 | Zaffaroni | 600/12 |
| 3,863,640 | 2/1975 | Haverstock | 606/216 |
| 4,197,840 | 4/1980 | Beck et al. . | |
| 4,799,487 | 1/1989 | Bleicher . | |
| 5,192,315 | 3/1993 | Jacob-LaBarre . | |
| 5,522,889 | 6/1996 | Baker et al. . | |
| 5,524,689 | 6/1996 | Clark . | |

FOREIGN PATENT DOCUMENTS

| | | |
|---|---|---|
| 2 278 314 | 2/1976 | France . |
| 23 35 475 | 6/1973 | Germany . |
| 23 63 563 | 6/1975 | Germany . |

*Primary Examiner*—Michael Powell Buiz
*Assistant Examiner*—Julian W. Woo
*Attorney, Agent, or Firm*—John P. O'Banion

[57] ABSTRACT

An apparatus for occluding the upper and lower eyelids of a patient at risk of developing corneal keratopathy. A magnet is attached to or placed within a polymer base that conforms to the normal curvature of the external skin surface of the human eyelid. The conforming base is then attached to the upper eyelid using a removable adhesive such as double-sided tape. A similar conforming base and magnet is attached to the lower eyelid. The magnetic attraction from the opposing magnets pulls the upper and lower eyelids together so as to close the eye, but can be broken by gently spreading apart the conforming bases for examination of the eye or application of medicaments when necessary. Variations of the device can be made where one of the magnets is replaced by a metal plate or other magnetic, or where a pair of electromagnets are used with a control for switching polarity to the electromagnets for reversal between magnetic attractive and repulsive forces and hence opening and closing the eyelids.

17 Claims, 5 Drawing Sheets

MAGNETIC EYELID OCCLUDING APPARATUS

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

1. Field of the Invention

This invention pertains generally to devices for maintaining eyelids in a closed position for medical treatment and more particularly to a magnetic eyelid closure apparatus that is easily attached to and removed from a patient's eyelids.

2. Description of the Background Art

Corneal exposure is a frequent source of ophthalmologic consultation and can result in significant morbidity. Currently, mild exposure keratopathy is treated using ocular lubricants, moisture chambers, and taping the eyelids shut. In severe cases, surgical procedures such as tarsorrhaphy and Frost suture are used.

Taping the eyelids shut fails for several reasons. First, the eyelid opening force is placed solely on the tape adhesive and the adhesive strength is eventually overcome. Second, once the eye is shut using tape, medication cannot be placed into the eye without removing the tape. This constant removal of tape can lead to skin breakdown and infection. Also, when eye lubricants are placed on the eye, tape adhesive will fail to adhere unless the external skin surface is thoroughly cleaned. Furthermore, a taped eye cannot be examined without tape removal.

The more radical approach of surgery is a definitive method of eyelid closure, and tarsorrhaphy and other surgical techniques have been used to close the eyelids when taping and lubricants have failed to protect the corneal surface. While surgical closure is effective, the procedure is invasive and expensive.

Various alternatives to taping and suturing eyelids closed can be seen from prior patents. For example, German No. 23 35 475 teaches implanting magnets directly beneath the skin in the eyelids of a patient, a method which is invasive and can lead to infection. French No. 2 278 314 shows the use of implantable magnets to hold the eyelids in the open position, where muscle tone is insufficient to do so. To address the problem of infection, as well as splintering of brittle magnets resulting from bending or stress, U.S. Pat. No. 4,197,840 teaches placing the magnets in a flexible, tissue-compatible, sealed enveloping body prior to implantation. U.S. No. Pat. No. 4,799,487 overcomes the problems associated with directly implanted magnets by implanting an electromagnet in the bone below the eye and a ferrous material in the eyelid. Each of these approaches, however, is invasive, expensive, and can lead to infection or other surgical complications. In addition, use of directly implanted magnets will intefere with x-rays, and MRI scans cannot be performed because they would place magnetic stress on the implants and potentially cause damage to the eyelids and/or the patient's eyes.

Therefore, there is a need for an inexpensive, easy to use, non-invasive method of maintaining the eyelids in a closed position that does not degrade with the use of lubricants and other medicaments, does not irritate or otherwise place stress on the patient's skin during use, and allows for the eyelids to be easily opened by medical personnel when necessary for examination or medication. The present invention satisfies those needs, as well as others, and overcomes the deficiencies found in prior devices and methods. The foregoing background art reflects the state of the art of which the applicant is aware and is tendered with the view toward discharging applicant's acknowledged duty of candor in disclosing information which may be pertinent in the examination of this application. It is respectfully stipulated, however, that none of these patents teach or render obvious, singly or when considered in combination, the applicant's invention as claimed herein.

BRIEF SUMMARY OF THE INVENTION

The present invention generally comprises a magnetic eyelid occluding apparatus that is attached to the external skin surface of the eyelids. By way of example, and not of limitation, the invention includes a pair of opposing eyelid occluders (magnocluders), one for the upper eyelid and one for the lower eyelid. Each eyelid occluder comprises a flexible or arcuate base that will conform to the arcuate shape of the eyelids, a lip projecting outward from the front face of the base, and a magnet carried by the lip. The magnet may be either attached to the surface of the lip or, preferably, embedded in the lip, with its poles generally perpendicular to the face of the lip. The magnets in the upper and lower eyelid occluders, however, must have their poles in a reverse orientation so that the magnets will attract when the surfaces of the lips oppose each other. In an alternative embodiment, only one eyelid occluder carries a magnet and the other magnocluder carries a metal place or other magnetic material. In still another embodiment, each eyelid occluder carries an electromagnet and a polarity control is used to cause the electromagnets to either attract or repel each other.

In use, the eyelid occluders are attached to the external surface of the eyelids using double-sided tape or other removable adhesive material attached to the rear face of the base and placed on clean dry skin. Once the upper occluder is attached to the upper eyelid and the lower occluder is attached to the lower eyelid the magnets will attract each other and hold the eyelids in a closed position. The eye can then be examined and eye lubricants can be placed in the eye by gently spreading apart the lips carrying the magnets.

Because the invention uses magnets to close the eyelids and the adhesive is used only to anchor the invention to the eyelids, the eyelid opening force is distributed primarily to the magnets. Medications and lubricants can then be placed in the eye by overcoming the magnetic attraction using a gentle spreading maneuver of the brow and upper cheek. Since the device is not removed prior to application of eye lubricants, the adhesive will maintain its adherence. The ability to open the eye easily permits frequent pupillary examinations or complete eye examinations without removal of the device.

An object of the invention is to provide an eyelid occlusion apparatus that is noninvasive.

Another object of the invention is to prove an eyelid occlusion apparatus that can be easily attached to and removed from the eyelids.

Another object of the invention is to provide an eyelid occlusion apparatus that attaches to the eyelids with an adhesive that remains in place when the eyelids are opened for examination or medicating.

Another object of the invention is to provide a noninvasive eyelid occlusion apparatus that remains in place when the eyelids are opened for examination or medicating.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
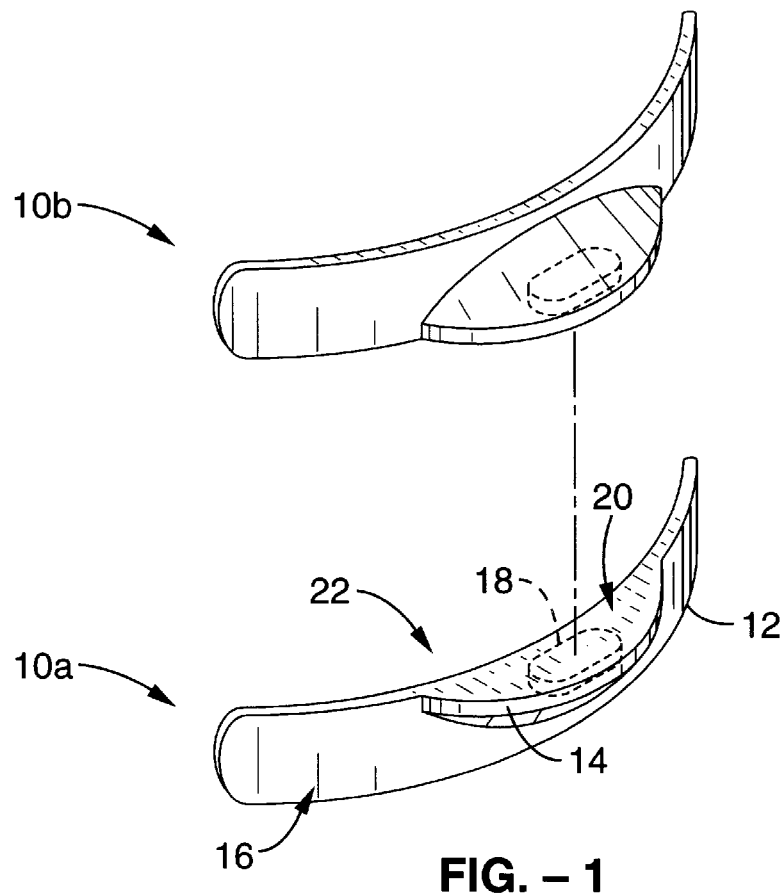
FIG. 1 is a perspective view of a pair of opposing eyelid occluders in accordance with the present invention wherein the magnets and/or magnetic materials are embedded.

Referring more specifically to the drawings, for illustrative purposes the present invention is embodied in the apparatus generally shown in FIG. 1 through FIG. 10, where like reference numerals denote like parts. It will be appreciated that the apparatus may vary as to configuration and as to details of the parts without departing from the basic concepts as disclosed herein.

Figure 2:
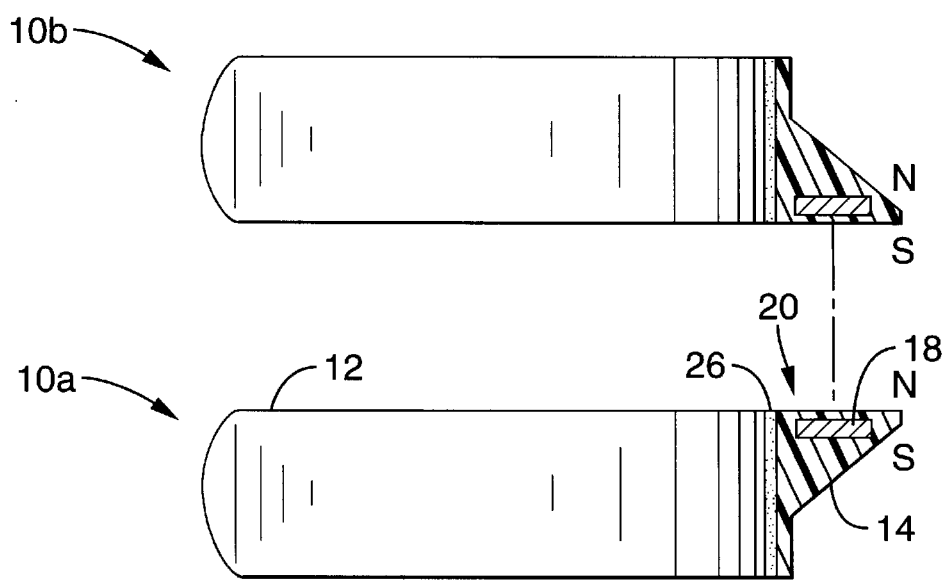
FIG. 2 is a side view in cross-section of the eyelid occluders shown in FIG. 1.
Figure 3:
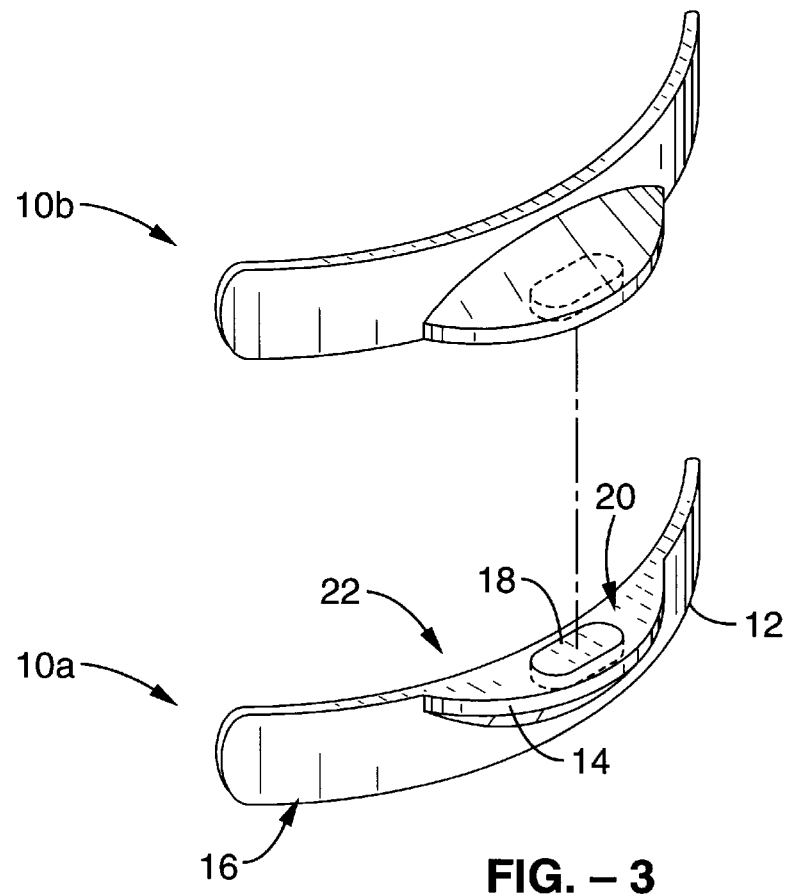
FIG. 3 is a perspective view of an alternative embodiment of the eyelid occluders shown in FIG. 1 wherein the magnets and/or magnetic materials are flush mounted.
Figure 4:
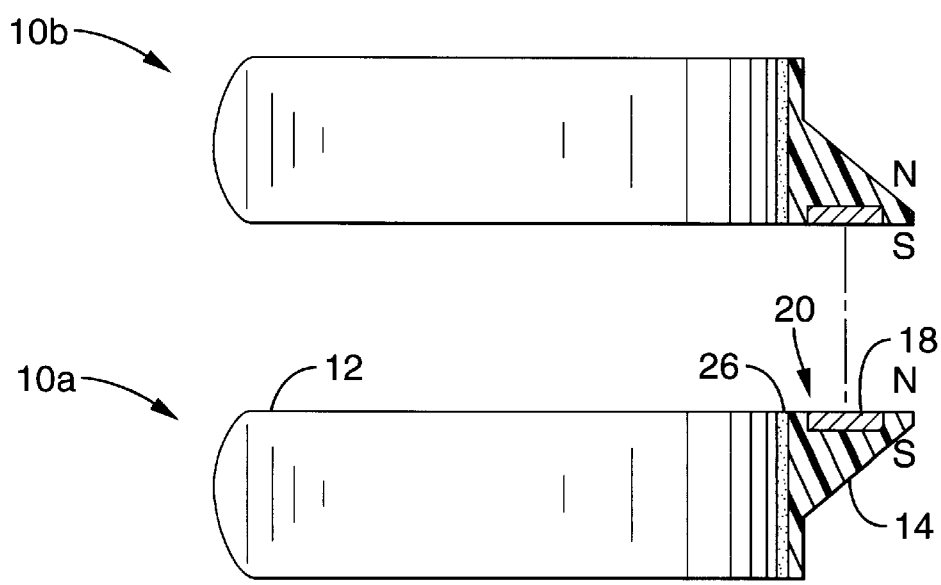
FIG. 4 is a side view in cross-section of the eyelid occluders shown in FIG. 3.
Figure 5:
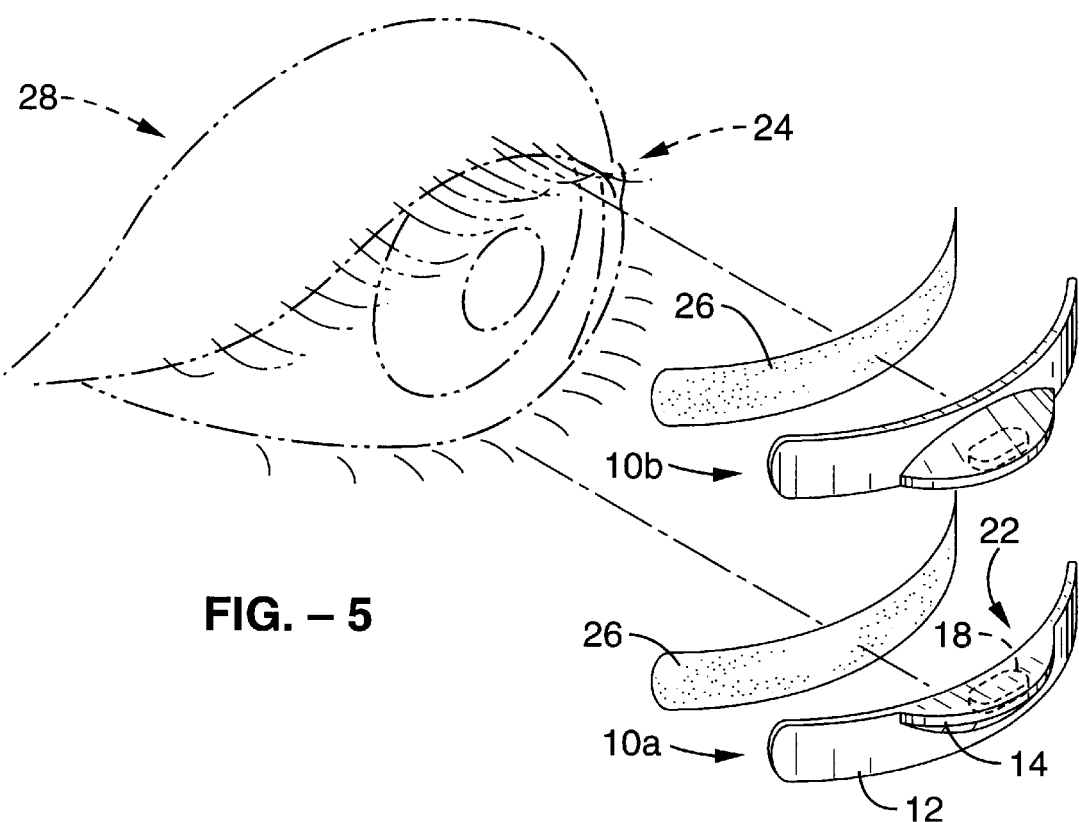
FIG. 5 is an exploded view of the eyelid occluders shown in FIG. 1 and FIG. 2 in relation to an eye and eyelids depicted in phantom.
Figure 6:
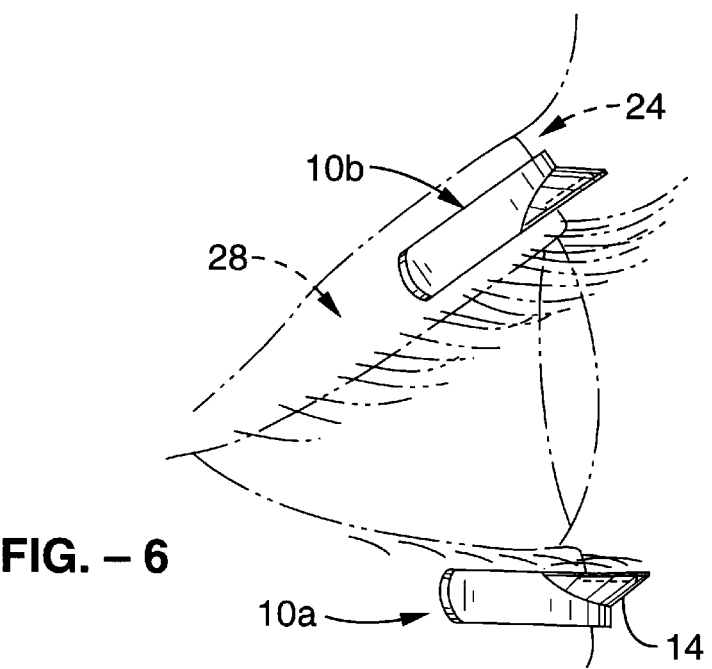
FIG. 6 is a side elevation view of the eyelid occluders shown in FIG. 1 and FIG. 2 shown attached to eyelids depicted in phantom.
Figure 7:
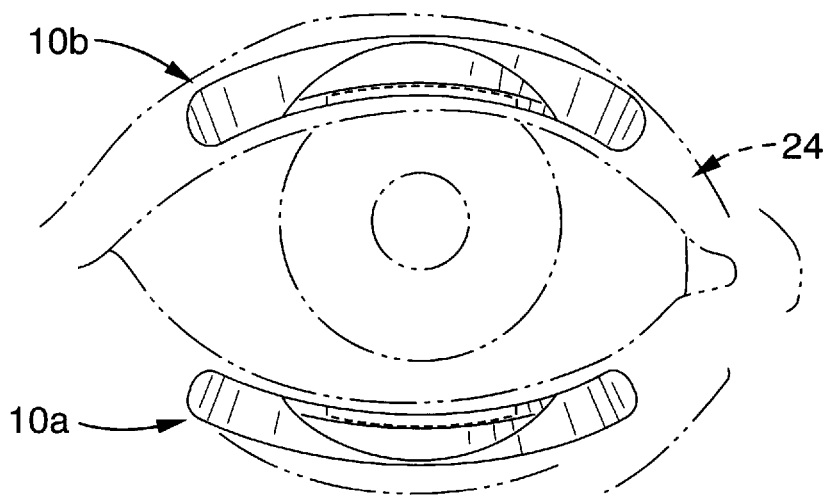
FIG. 7 is a front view of the assembly shown in FIG. 6.

Referring first to FIG. 1 through FIG. 4, a pair of opposing eyelid occluders 10a, 10b are shown. Each eyelid occluder 10 comprises a base 12 that will conform to the arcuate shape of the eyelids, a lip 14 projecting outward from the front face 16 of the base 12, and a magnet 18 carried by the lip 14. Base 12 can be fabricated from a lightweight polymer material that is sufficiently flexible to conform to the shape of the eyelid or from a rigid polymer material that is arcuately shaped as shown. The magnet 18 is preferably embedded in the lip 14 with its poles oriented generally perpendicular to the face 20 of the lip 14 as shown in FIG. 1 and FIG. 2. Alternatively, magnet 18 could be surface mounted or flush mounted as shown in FIG. 3 and FIG. 4. Lower 10a and upper 10b eyelid occluders are substantially identical in construction except that the magnets must have their north and south poles in a reverse orientation as indicated on the drawings so that the magnets will exert an attractive force on each other when the faces 20 of lips 14 are opposite each other. While polymers and the like are preferred materials for fabrication of the invention, the device can alternatively be fabricated from cardboard, stiff paper or other materials that will to conform to the shape of the eyelid while being sufficiently rigid to support a magnet or magnetic material.

Figure 8:
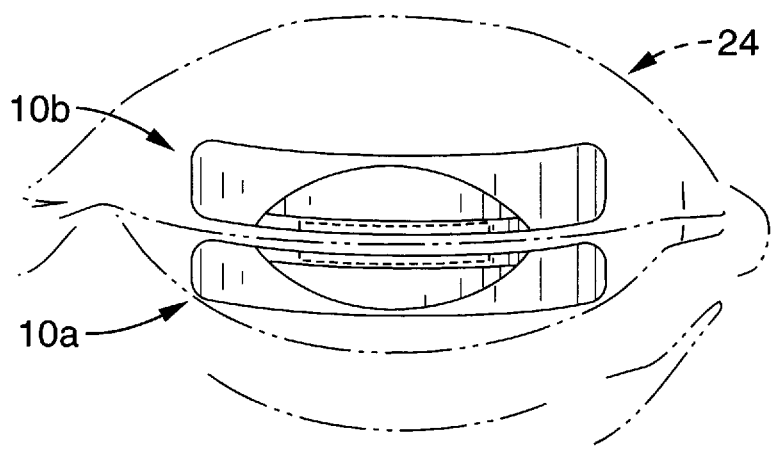
FIG. 8 is a front view of the assembly shown in FIG. 6 with the eyelids shown in an occluded position.

Referring to FIG. 2, and FIG. 5 through FIG. 8, an eyelid occluder 10 in accordance with the invention is attached to an eyelid 24 using double-sided tape 26 or other removable adhesive (FIG. 2 and FIG. 8) positioned between the rear face 22 of conforming base 12 and a clean, dry section of the external skin surface 28 of the eyelid 24. Preferably, the edge of confirming base 12 should be positioned approximately 0.5 to 1.0 mm away from the edge of the eyelid as shown so that there is no risk of lip 14 (or a surface mounted magnet carried by lip 14) from scratching the cornea. Once the upper occluder is attached to the upper eyelid and the lower occluder is attached to the lower eyelid the magnets will attract each other and hold the eyelids in a closed position as shown in FIG. 8. The eye can then be examined or eye lubricants can be placed in the eye by gently spreading apart the lips carrying the magnets.

The force of the magnets should be selected such the eyelids will be maintained in a closed position without risk that the attractive force can be overcome by the normal eye opening muscular force of the patent while still allowing for the force to be broken by gently spreading apart the magnets for examination or treatment of the eye. Those skilled in the art will appreciate that, by choosing a sufficiently strong magnet, an alternative embodiment of the invention could be fabricated where only one eyelid occluder carries a magnet and the other eye occluder carries a metal place or other magnetic material. Those skilled in the art will also appreciate that the exact size and shape of eye occluder 10, conforming base 12, lip 14 and magnet 18 can be varied so long as the base will conform to the shape of the eyelid when attached and the magnets will maintain the eyelids in a closed position. The exact materials used can also be varied, although a lightweight polymer such as plastic is preferred.

Figure 9:
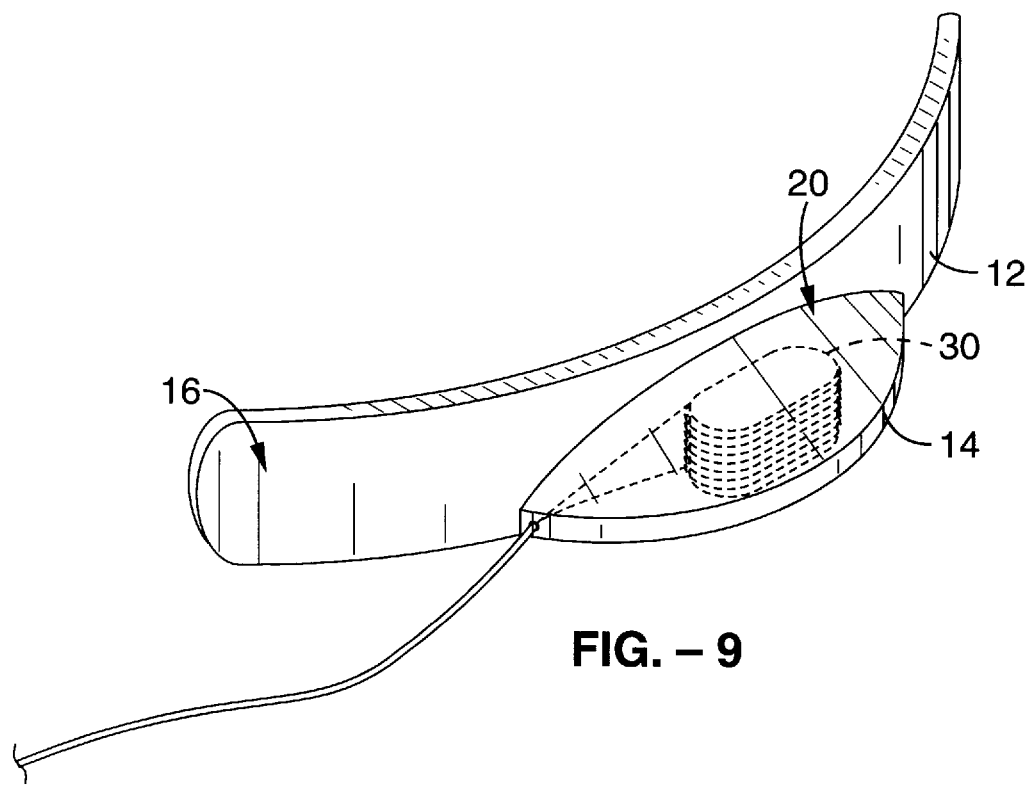
FIG. 9 is a perspective view of an alternative embodiment of an eyelid occluder in accordance with the present invention wherein an electromagnet is used.
Figure 10:
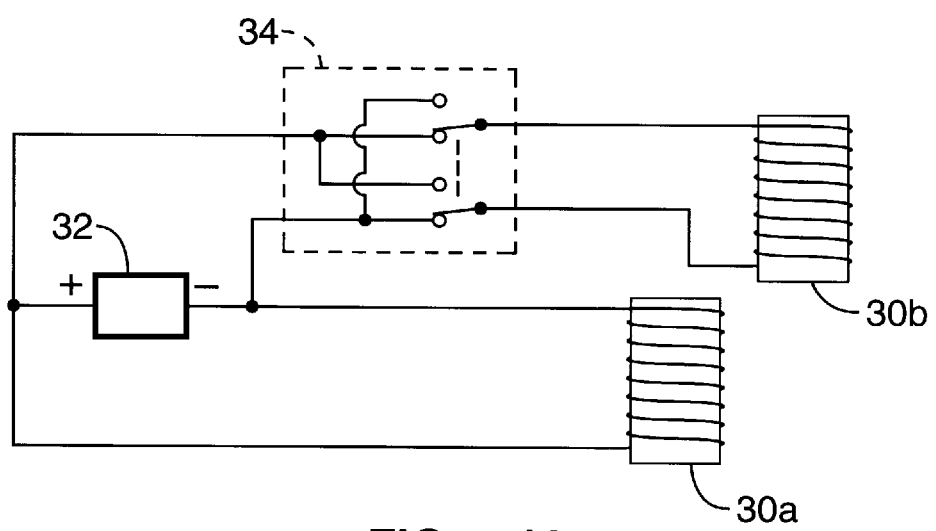
FIG. 10 is a schematic diagram showing a polarity reversal circuit for use with a pair of the electromagnetic eyelid occluders shown in FIG. 9.

Referring now to FIG. 9 and FIG. 10, an alternative embodiment of an eyelid occluder is shown. In the embodiment shown, lip 14 carries an electromagnet 30 instead of a permanent magnet and electromagnet 30 would be coupled to direct current power supply 32. By placing an electromagnet in both the upper and lower eyelid occluders, a switch 34 can be provided to allow the user to control the polarity to the electromagnets and select whether the electromagnets will attract or repel each other.

The present invention has many applications. For example, an intensive care unit would be an ideal environment for the invention. Metabolic derangement, artificial respirators, immunologic dysfunction, impaired mental status, and facial injuries can leave a patient vulnerable to numerous ophthalmologic catastrophes. A significant population of patients in intensive care units have some form of superficial corneal abnormality. Many of those patients are obtunded or pharmacologically paralyzed, placing them at a high risk for corneal exposure due to inadequate lid closure and/or decreased blinking response. The present invention could prevent the development of corneal abnormalities and decrease the need for frequent applications of expensive ocular lubricants. Nursing care would be simplified and hospital costs lowered.

In addition, the invention could be used in out-patient care. For example, many individuals with facial nerve palsy, such as Bells palsy, could benefit. The invention could be used while sleeping for complete eyelid closure. This would allow for excellent corneal protection throughout the night. There would be no need for a large, uncomfortable strip across the eye, and the patient could open the eye without removing the invention if vision through the eye was necessary.

Accordingly, it will be seen that this invention provides a noninvasive, easy to use, inexpensive, and removable eyelid occlusion device. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus attachable to the external skin surfaces of upper and lower eyelids for maintaining eyelids in a closed position, comprising:
   (a) a first support member for attachment to the external skin surface of a first eyelid;
   (b) a second support member for attachment to the external skin surface of a second eyelid opposing said first eyelid;
   (c) a magnet carried by said first support member; and
   (d) a magnetic material carried by said second support member.

2. An apparatus as recited in claim 1, further comprising adhesive means for detachably coupling said first and second support members to said external skin surfaces of said eyelids.

3. An apparatus as recited in claim 1, wherein said magnetic material carried by said second support member comprises a second magnet.

4. An apparatus as recited in claim 3, wherein opposing poles of said magnets are aligned for magnetic coupling when said support members are attached to said external skin surfaces of said eyelids.

5. An apparatus as recited in claim 1, wherein each said support member comprises an eyelid conforming base having a outer face, and inner face, and a lip projecting outward from said outer face.

6. An apparatus as recited in claim 5, wherein said magnet is attached to said lip of said first support member, and said magnetic material is attached to said lip of said second support member.

7. An apparatus as recited in claim 6, wherein said magnetic material carried by said second support member comprises a second magnet and wherein opposing poles of said magnets are aligned for magnetic coupling when said support members are attached to said external skin surfaces of said eyelids.

8. An apparatus as recited in claim 5, wherein said adhesive means is applied to said inner faces of said eyelid conforming bases.

9. A magnetic eyelid closing apparatus, comprising:
   (a) a first eyelid occluder;
   (b) a second eyelid occluder;
   (c) means for magnetically coupling said first and second eyelid occluders; and
   (d) adhesive means for detachably coupling said eyelid occluders to external skin surfaces of eyelids.

10. An apparatus as recited in claim 9, wherein said means for magnetically coupling said first and second eyelid occluders comprises:
    (a) a magnet attached to said first eyelid occluder; and
    (b) a magnetic material attached to said second eyelid occluder.

11. An apparatus as recited in claim 9, wherein said magnetic material comprises a second magnet.

12. An apparatus as recited in claim 11, wherein opposing poles of said magnets are aligned for magnetic coupling when said eyelid occluders are attached to said external skin surfaces of said eyelids.

13. An apparatus as recited in claim 9, wherein each said eyelid occluder comprises an eyelid conforming base having a outer face, and inner face, and a lip projecting outward from said outer face.

14. An apparatus as recited in claim 13, wherein said magnet is attached to said lip of said first eyelid occluder, and said magnetic material is attached to said lip of said second eyelid occluder.

15. An apparatus as recited in claim 13, wherein said magnetic material carried by said second eyelid occluder comprises a second magnet and wherein opposing poles of said magnets are aligned for magnetic coupling when said eyelid occluders are attached to said external skin surfaces of said eyelids.

16. An apparatus as recited in claim 13, wherein said adhesive means is applied to said inner faces of said eyelid occluders.

17. An eyelid occlusion apparatus for attachment to upper and lower eyelids, comprising:
    (a) a first base capable of conforming to the shape of the upper eyelid;
    (a) a second base capable of conforming to the shape of the lower eyelid;
    (c) a first lip projecting outward from said first base;
    (d) a second lip projecting outward from said second base;
    (e) a first magnet attached to said first lip; and
    (f) a second magnet attached to said second lip;
    (g) wherein opposing poles of said magnets are aligned for magnetic coupling when said bases are attached to external skin surfaces of opposing eyelids.

* * * * *